United States Patent [19]

Hilpert

[11] Patent Number: 5,512,682
[45] Date of Patent: Apr. 30, 1996

[54] NITRILE COMPOUNDS USEFUL AS INTERMEDIATES IN THE PRODUCTION OF BETA AMINO ALCOHOLS

[75] Inventor: Hans Hilpert, Reinach, Switzerland

[73] Assignee: Hoffmann-La Roche Inc., Nutley, N.J.

[21] Appl. No.: 401,583

[22] Filed: Mar. 9, 1995

Related U.S. Application Data

[62] Division of Ser. No. 208,420, Mar. 9, 1994, Pat. No. 5,455,353.

[30] Foreign Application Priority Data

Mar. 24, 1993 [CH] Switzerland ................. 896/93

[51] Int. Cl.$^6$ ................................. C07D 209/48
[52] U.S. Cl. ................................. 548/477
[58] Field of Search ................. 548/110, 478, 548/479, 477

[56] References Cited

U.S. PATENT DOCUMENTS

| | | | |
|---|---|---|---|
| 4,374,829 | 2/1983 | Harris et al. | 424/177 |
| 4,462,943 | 7/1984 | Petrillo, Jr. et al. | 260/112.5 |
| 5,157,041 | 10/1992 | Handa et al. | 514/314 |
| 5,236,783 | 10/1993 | Gokhale et al. | 514/314 |

FOREIGN PATENT DOCUMENTS

| | | | |
|---|---|---|---|
| 0156279 | 10/1985 | European Pat. Off. | 548/232 |
| 0432695 | 6/1991 | European Pat. Off. | 546/146 |
| 0543343 | 5/1993 | European Pat. Off. | 564/300 |

OTHER PUBLICATIONS

Melon, et al, Enantiomerically pure 3-amino-2-hydroxy and 5-amino-4-hydroxy acids from D-isoascorbic acid, Bull Soc. Chim Fr, vol. 129, pp. 585–593 (1992).

Iizuka, et al, Orally Potent Human Renin Inhibitors Derived from Angiotensinogen Transition State: Design, Synthesis, and Mode of Interaction, J. Med. Chem. vol. 33, pp. 2707–2714 (1990).

*Primary Examiner*—C. Warren Ivy
*Assistant Examiner*—Zinna N. Davis
*Attorney, Agent, or Firm*—George M. Gould; William H. Epstein; Catherine A. Picut

[57] ABSTRACT

Nitriles of formula

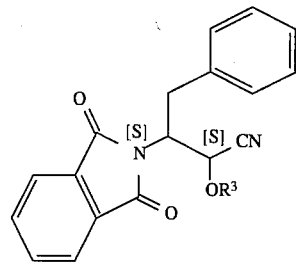

wherein R3 is acetoxy or benzyloxycarbonyl, useful as intermediates in the production of beta-aminoalcohols.

2 Claims, No Drawings

NITRILE COMPOUNDS USEFUL AS INTERMEDIATES IN THE PRODUCTION OF BETA AMINO ALCOHOLS

This is a division of application Ser. No. 08/208,420 filed Mar. 9, 1994, U.S. Pat. No. 5,455,353.

SUMMARY OF THE INVENTION

The present invention is concerned with a novel process for the production of the β-aminoalcohol 2-[3(S)-amino-2(R)-hydroxy-4-phenylbutyl] -N-tert.butyl-decahydro-(4aS, 8aS)-isoquinoline-3(S)-carboxamide of the formula,

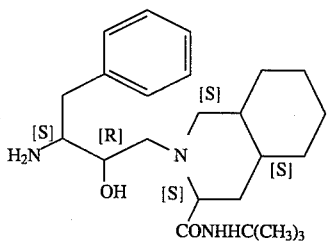

This β-aminoalcohol is useful as an intermediate in the chemical synthesis of certain amino acid derivatives that can be used in the prophylaxis or treatment of retro-viral infections, such as HIV. (See British Patent Application No. 8908035 and corresponding U.S. Ser. No. 07/362,621 now U.S. Pat. No. 5,157,041. See also, U.S. application Ser. No. 08/128,978) now U.S. Pat. No. 5,451,678.

The invention is also directed to novel intermediates occurring in said process for the production of this β-aminoalcohol.

The process of producing the β-aminoalcohol of formula 10 in accordance with the invention comprises first forming a reaction mixture by reacting a sulphonic acid ester of formula,

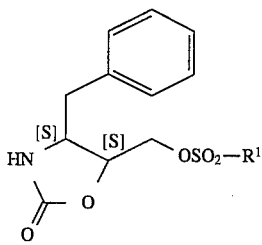

wherein $R^1$ is lower-alkyl or phenyl,
with N-tert.butyl-decahydro-(4aS,8aS)-isoquinoline-3(S)-carboxamide of formula,

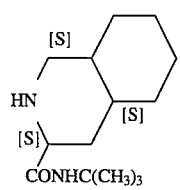

in the presence of a base to produce an oxazolidinone of formula,

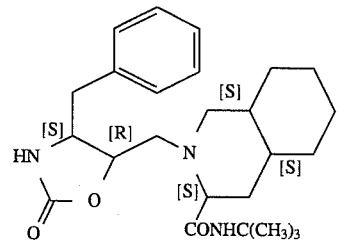

The oxazolidinone of formula 9 in the reaction mixture in which it is formed is then treated with a strong acid to convert this oxazolidinone of formula 9 to its readily crystalizing salt so that the oxazolidinone may be purified. Then, any sulphonic acid remaining in the reaction mixture is removed by treating said reaction mixture with a base. Next, the oxazolidinone of formula 9, or salt thereof, in the reaction mixture, is cleaved by refluxing the reaction mixture with another base to produce the aminoalcohol of formula 10 above.

DETAILED DESCRIPTION OF THE INVENTION

As used herein, aminoalcohol refers to a compound having both amino and alcohol groups. The term lower-alkyl alone or in combination, e.g., lower-alkanol, denotes straight chain or branched hydrocarbons with 1 to 6 carbon atoms, preferably with 1 to 4 carbon atoms.

The compounds 8 and 10 above correspond to those of formulae "VII" and, "II", respectively, in EPA-0432695 where they are described as intermediates in the production of therapeutically active products.

As used in formula VII, $R^1$ may be lower alkyl or phenyl. When $R^1$ is phenyl, the phenyl may be unsubstituted or substituted. When substituted, the phenyl may be substituted in one or more sites, preferably one or two sites. Any conventional substitution group may be used, such as halogens, lower-alkyls, or nitro groups. When the substitution group is halogen, any halogen may be used, such as chlorine, bromine or fluorine.

The reaction of a sulphonic acid ester of formula VII with the amide of formula 8 is conveniently carried out in a solvent in the presence of a base to produce the oxazolidone of formula 9. Any inert organic solvent may be used, such as dimethylsulfoxide (DMSO) or a hydrocarbon, such as toluene, or triethylamine, a lower-alkanol, or a ketone, where the preferred lower-alkanol is ethanol, and the preferred ketone is 4-methyl-2-pentanone. Any base may be used to react a sulfonic acid ester of formula VII with the amide of formula 8, such as a lower-alkylamine, e.g., triethylamine, or an alkali metal carbonate, e.g., sodium carbonate.

The reaction of a sulphonic acid ester of formula VII with the amide of formula 8 is carried out while heating said ester and amide to the reflux temperature, which temperature is preferably from about 50° C. to about 150° C. Best results are achieved when said ester and amide is heated to a temperature of 80°–110° C. In order to purify the oxazolidinone of formula 9, the oxazolidininone is converted into a readily crystallizing acid-addition salt such as a sulphonate. The preferred sulphonates are p-tolyl-, p-bromphenyl- or p-nitrophenylsulphonate. These sulphonates are prepared by the addition of a strong acid such as sulphuric acid or preferably hydrochloric acid to the oxazolidinone 9.

The sulphonic acid is removed from the reaction mixture by treating the reaction mixture with a base in the presence of a solvent. Any base and any solvent may be used to remove the sulphonic acid. The preferable base is sodium bicarbonate. The preferred solvent is ethyl acetate. After the sulphonic acid is removed, the oxazolidinone 9 in the reaction mixture is conveniently cleaved by refluxing it in the presence of a base, such as NaOH or KOH. The reflux temperature is preferably in the range of from about 20° C. to about 100° C. Best results are obtained when the reaction mixture is heated to 80° C. Cleaving the oxalidinone 9 with a base is carried out in the presence of a solvent. Any inert solvent may be used as the reaction medium, such as water, ethanol, or a mixture thereof. In this manner, the aminoalcohol of formula 10 is produced.

The above sulphonic acid esters of formula VII are prepared in accordance with this invention by treating an α-hydroxy-β-amino acid ester of formula,

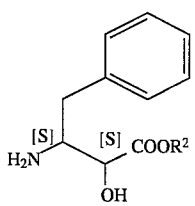

IV wherein $R^2$ is lower-alkyl,
or an acid-addition salt thereof, in the presence of a solvent with a carbonylating agent to cyclize said ester or salt thereof to produce 2-oxo-oxazolidine- 5-carboxylic acid ester of formula,

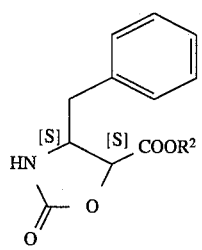

V wherein $R^2$ is as above.

Next, the carbo-lower alkoxy group of formula V above is reduced in the presence of an inert organic solvent to produce (4S,5S)-4-benzyl-5 -hydroxymethyl-oxazolidin-2-one of the formula,

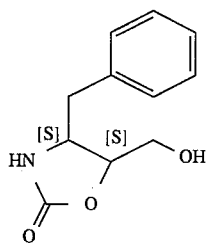

6

The compound of formula 6 is then treated with a sulphonyl chloride of formula $R^1$—$SO_2Cl$, wherein $R^1$ is lower-alkyl or phenyl which may be substituted or unsubstituted, in the presence of a base to produce the sulphonic acid ester of formula VII. When $R^1$ is lower alkyl, methyl, ethyl and isopropyl are examples thereof.

Any acid-addition salt of the α-hydroxy-β-amino acid ester may be used to react with a carbonylating agent to produce a compound of formula V. Examples of salts of the α-hydroxy-β-amino acid ester IV are those formed by reacting said ester with an acid, such as acetic acid or sulphuric acid.

Any conventional carbonylating agent may be used to convert α-hydroxy-β-amino acid ester of formula IV, or salt thereof, to a compound of formula V. The preferred carbonylating agents are carbonyldiimidazole, phenyl chloroformate, triphosgene and preferably phosgene. The carbonylation of IV or a salt thereof is conveniently carried out in a solvent. Any inert organic solvent may be used, such as $CH_2Cl_2$, toluene or preferably tetrahydrofurane (THF). Said carbonylation is carried out at a temperature between −10° C. and +50° C. The preferred temperature for carbonylation is between 0° C. and 20° C. The carbonylating step may optionally be carried out in the presence of a base such as triethylamine, $K_2CO_3$ or $NaHCO_3$.

The reduction of the 2-oxo-oxazolidine-5-carboxylic acid ester V is conveniently carried out in the presence of a solvent using sodium bis(2-methoxyethoxy)aluminium hydride, $LiAlH_4$ or preferably $NaBH_4$. Any inert organic solvent may be used, such as toluene, THF or preferably ethanol may be used. The temperature for said reaction is not critical, but is preferably between 0° C. and 60° C. Best results are obtained when the temperature for reducing the ester of formula V is 22° C.

The treating of the alcohol of formula 6 with a sulphonyl chloride is carried out in a solvent in the presence of a base. Any solvent may be used as the reaction medium, such as ethyl acetate, acetone or THF. Best results are obtained when the solvent is THF. Any base may be used, such as triethylamine or preferably N-methylmorpholine. The temperature is not critical but it is preferable to carry out said treating at a temperature between 0° C. and 60° C. Best results are obtained at a temperature between 20° C. and 40° C.

The above α-hydroxy-β-amino acid esters IV used to produce a compound of formula VII, can be prepared in accordance with the invention by cyanolating 3-phenyl-2(S)-phthalimidopropan-1-al of formula,

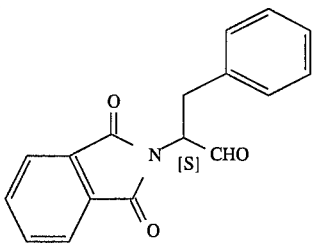

1 into the 1-cyano-3-phenyl-2(S)-phthalimidopropan-1-ol derivative of formula,

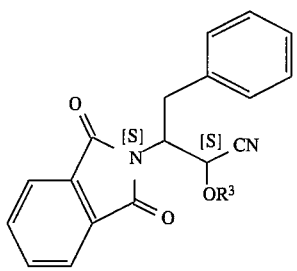

II wherein $R^3$ is hydrogen, lower-alkanoyl, benzyloxycarbonyl or tri(lower-alkyl)silyl.

Any tri(lower-alkyl)silyl group present in the nitrile of formula II is cleaved by treating said nitrile with an acid to produce a nitrile of formula II wherein $R^3$ is hydrogen. Next, the nitrile of formula II is treated with a strong acid in the presence of a lower alkanol $R^2$—OH, wherein $R^2$ is as above, to convert said nitrile into an acid-addition salt of the imino ether of formula,

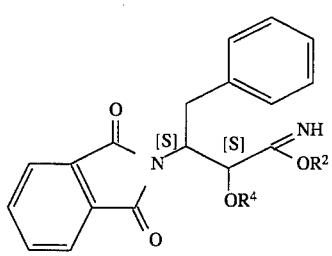

II' wherein R⁴ is hydrogen, lower-alkanoyl or benzyloxycarbonyl and R² is lower-alkyl.

This acid-addition salt of the imino ether of formula II' may be isolated and then hydrolyzed to produce an α-hydroxy acid ester of the formula,

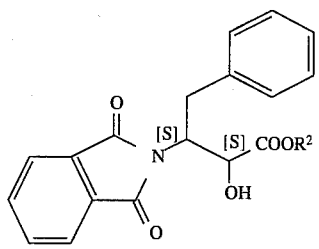

III wherein R² is as above.

The compound of formula III can then be converted into the α-hydroxy-β-amino acid ester of formula IV by treating it firstly with a base and then with a strong acid.

Any tri(lower-alkyl)silyl group may be used. The preferred silyl group is trimethylsilyl.

For the preparation of a nitrile II in which R³ is hydrogen, a reaction mixture is produced by treating a solution of the aldehyde of formula 1, in the presence of a solvent with aqueous sodium pyrosulphite. Any inert organic solvent may be used as the reaction medium. The preferred solvent is toluene. The resulting reaction mixture is then treated with NaCN, optionally in a solvent such as water, aqueous dichloromethane or aqueous toluene. In a variant, a reaction mixture of the aldehyde 1 and $ZnBr_2$ is formed in a solvent, such as $CH_2Cl_2$ and the reaction mixture is reacted with trimethylsilyl cyanide at a temperature from about −70° C. to about 0° C. to produce a silyl ether of the cyanohydrin. The silylether is then cleaved by the addition of a solution of citric acid in ethanol to produce a nitrile of formula II, in which R³ is hydrogen.

For the preparation of a nitrile II in which R³ is lower-alkanoyl, e.g. acetyl, a reaction mixture is produced by treating a solution of the aldehyde 1 with the corresponding acid anhydride, e.g., acetic anhydride, in a solvent such as $CH_2Cl_2$. The resulting reaction mixture is treated with NaCN in the presence of benzyltriethylammonium chloride while cooling conveniently to −10° C. to 0° C.

For the preparation of a nitrile II in which R³ is benzyloxycarbonyl, an analogous procedure is followed, but using benzyl chloroformate in place of an acid anhydride.

The nitrile II in which R³ is hydrogen can be also obtained by hydrogenating the nitrile II in which R³ is benzyloxycarbonyl in a solvent such as ethanol or $CH_2Cl_2$.

The strong acid used to convert the nitrile II to the salt of the imino ether of formula II' may be any strong acid. Best results are obtained when the strong acid is HCl. Any solvent may be used such as a lower-alkanol, $CH_2Cl_2$, toluene, t-butyl methyl ether and the like. The preferred solvent is a mixture of $CH_2Cl_2$ and a lower alkanol or a mixture of toluene and a lower alkanol. The temperature for converting nitrile II to II' is not critical. Best results are obtained when treating the nitrile II with a strong acid while cooling to −10° C. to +10° C., conveniently to 0° C.

Hydrolyzing the salt of the imino ether of formula II' to the hydroxy acid ester III is carried out in the presence of a solvent, such as aqueous ethyl acetate, $CH_2Cl_2$, or preferably in the presence of a mixture of an aqueous toluene and a lower alkanol.

The isomers of the salt of the (S,S)-imino ether of formula II' may be separated by crystallization of the salt. The isomers of the α-hydroxy acid ester of formula III may also be separated by crystallization. When $CH_2Cl_2$ is used as the solvent during such crystallization of II' or III, the isomer purity is within the range of 93–99%. When toluene is used as the solvent, it is not possible to separate the isomers of the salt of II'. Isomers of compound IV and 6 can also be separated by crystallization, wherein an enrichment up to 92% and 99%, respectively, of desired isomers is achieved. All compounds III can also be separated by chromotography on $SiO_2$.

The compound of formula IV is obtained by treating a compound III firstly with a base and then with a strong acid. Any base may be used. The preferred base is methylamine. Likewise, any strong acid may be used, e.g., preferred strong acid is HCl. Treating IV with a base and a strong acid is carried out in sequence in the presence of a solvent such as THF or preferably an alcohol such as a lower alkanol, especially methanol. The temperature for such treating is not critical; however, the preferred temperature is −10° to +20° C. Best results are obtained when the treating with a base is carried out at 0° C., and the treating with a strong acid is carred out at 20° C.

The aldehyde starting material 1 is obtained by heating L-phenylalanine with phthalic anhydride in toluene, reacting the resulting N-protected L-phenylalanine with oxalyl chloride in toluene and catalytic amounts of DMF, followed by catalytic (Pd/C) hydrogenation of the resulting acid chloride corresponding to the desired aldehyde 1 in the presence of 1,2-butylene oxide in toluene.

EXAMPLE 1

(VII+8→9, R¹=p-NO₂C₆H₄)
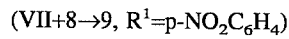

A) A suspension of 24.69 g of p-nitrobenzenesulphonic acid (4S, 5S)-4-benzyl-2-oxo-oxazolidin-5-ylmethyl ester (Example 12), 15.0 g of N-tert.butyl-decahydro-(4 aS,8aS)-isoquinoline-3(S)-carboxamide and 10.0 g of sodium carbonate in 76 ml of 4-methyl-2-pentanone is heated under reflux for 10 hours while stirring. The suspension is cooled to 80° C., diluted with 176 ml of 4-methyl-2-pentanone and 54 ml of 3N hydrochloric acid, cooled to 40° C. and filtered. The residue is washed with water and 4-methyl-2-pentanone and dried to give 35.1 g (88%) of (3S,4aS,8aS)-2-[(4S,5R)-4-benzyl-2-oxo-oxazolidin-5-ylmethyl] -N-tert.butyl-decahydro-isoquinoline-3-carboxamide p-nitrobenzene-sulphonate, $[α]_D^{20}=−31.2°$ (1% in DMF).

B) The same salt is obtained in 89% yield using triethylamine (2 equivalents) in place of sodium carbonate.

EXAMPLE 2

(VII+8→9, R¹=CH₃)
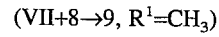

Analogously to Example 1B), by reacting 14 g of methanesulphonic acid (4S,5S)-4-benzyl-2-oxo-oxazolidin-5-ylmethyl ester (Example 9) with 11.7 g of N-tert.butyl-decahydro-(4aS,8aS)-isoquinoline-3(S)-carboxamide there are obtained, after the addition of 1 equivalent of p-tolylsulphonic acid, 11.8 g (40%) of (3S,4aS,8aS)-2-[(4S,5R)-4-benzyl- 2-oxo-oxazolidin-5-ylmethyl]-N-tert.butyl-decahydro-isoquinoline-3-carboxamide p-tolylsulphonate, m.p. 203°–205° C.

EXAMPLE 3

(VII+8→9, $R^1$=p-tolyl)

Analogously to Example 1B), by reacting 7.2 g of p-toluenesulphonic acid (4S,5S)-4-benzyl-2-oxo-oxazolidin-5-ylmethyl ester (Example 11) with 4.8 g of N-tert.butyl-decahydro-(4aS,8aS)-isoquinoline- 3(S)-carboxamide there are obtained 5.4 g (45%) of (3S,4aS,8aS)-2-[(4S,5R)-4-benzyl-2-oxo-oxazolidin-5-ylmethyl] -N-tert.-butyl-decahydro-isoquinoline-3-carboxamide p-tolylsuphonate, m.p. 202°–204° C.

EXAMPLE 4

(VII+8→9, $R^1$=p-BrC$_6$H$_4$)

Analogously to Example 1B), by reacting 30 g of p-bromobenzenesulphonic acid (4S,5S)-4-benzyl-2-oxo-oxazolidin-5-ylmethyl ester (Example 13) with 16.8 g of N-tert.butyl-decahydro-(4aS,8aS)-isoquinoline- 3(S)-carboxamide there are obtained 36.5 g (78%) of (3S,4aS,8aS)-2-[(4S,5R)-4-benzyl-2-oxo-oxazolidin-5 -ylmethyl-N-tert.butyl-decahydro-isoquinoline-3-carboxamide p-bromophenylsulphonate $[\alpha]_D^{20}$: –29.9° (1% in DMF).

EXAMPLE 5

(VII+8→9, $R^1$=o-NO$_2$C$_6$H$_4$)

Analogously to Example 1B), by reacting 39.2 g of o-nitrobenzenesulphonic acid (4S,5S)-4-benzyl-2-oxo-oxazolidin-5-ylmethyl ester (Example 10) with 23.8 g of N-tert.butyl-decahydro-(4aS,8aS)-isoquinoline- 3(S)-carboxamide there are obtained, after the addition of 1 equivalent of p-tolylsuphonic acid, 42 g (70%) of (3S,4aS,8aS)-2-[ (4S,5R)-4-benzyl-2-oxo-oxazolidin-5-ylmethyl]-N-tert.butyl-decahydro-isoquinoline- 3-carboxamide p-tolylsuphonate, $[\alpha]_d^{20}$: –34.2° (1% in DMF).

EXAMPLE 6

(9→10)

34.7 g of the salt product from Example 1 are partitioned between 110 ml of ethyl acetate and 110 ml of saturated sodium bicarbonate. The aqueous phase is extracted with ethyl acetate and the ethyl acetate extract is washed with 110 ml of saturated sodium bicarbonate and with water. The organic extracts are evaporated, the residue is diluted with 55 ml of ethanol and treated with a solution of 11.0 g of sodium hydroxide in 55 ml of water while stirring. The mixture is heated under reflux for 5 hours, diluted with 55 ml of H$_2$O and cooled to 22° C. The suspension is filtered and the residue is washed with water until the filtrate has a neutral pH. The residue is dried to give 20.7 g (93%) of 2-[3(S)-amino-2(R)-hydroxy-4-phenylbutyl]-N-tert.butyl-decahydro-( 4aS,8aS)-isoquinoline-3(S)-carboxamide, m.p. 175°–176° C.

EXAMPLE 7

(IV→V)

A) 39 g of phosgene are conducted into a suspension of 43 g of a 92:8 mixture of the (2S,3S) and (2R,3S) isomers of methyl 3-amino-2-hydroxy- 4-phenyl-butyrate acetate (Example 23B) in 350 ml of THF at 0° C. After stirring at 0° C. for 1 hour and at 22° C. for 24 hours the solution is concentrated to dryness, the residue is dissolved in 200 ml of CH$_2$Cl$_2$ and washed with water and saturated NaHCO$_3$. The aqueous phases are extracted with CH$_2$Cl$_2$ and the combined CH$_2$Cl$_2$ phases are dried and filtered. The filtrate is evaporated to give a crude 92:8 mixture of the (4S,5S) and (4S,5R) isomers of methyl 4-benzyl-2-oxo-oxazolidine-5-carboxylate. TLC (SiO$_2$, ethyl acetate): $R_f$=0.5. Yield 100%.

B) Analogously to Example 7A), by reacting a 98:2 mixture of the (2S,3S) and (2R,3S) isomers of methyl 3-amino-2-hydroxy-4-phenylbutyrate acetate (Example 23A) there is obtained a crude 98:2 mixture of the (4S,5S) and (4S,5R) isomers of methyl 4-benzyl-2-oxo-oxazolidine-5-carboxylate in 100% yield. TLC (SiO$_2$, ethyl acetate): $R_f$= 0.5.

EXAMPLE 8

(V→6)

A) 150 g of the 98:2 mixture of (4S,5S) and (4S,5R) isomers of methyl 4-benzyl-2-oxo-oxazolidine-5-carboxylate from Example 7B) are added at 15°–20° C. over 1.5 hours to a stirred solution of 20.8 g of NaBH$_4$ in 360 ml of ethanol and stirred for 2 hours. The suspension is treated with 540 ml of water at 20° C. and the pH is brought to 7 with 165 ml of 3N hydrochloric acid. The suspension is stirred at 22° C. for 2.5 hours, left to stand at 4° C. for 18 hours, then filtered and the residue is washed with water and dried to give 111.6 g (84%) of 99% (4S,5S)-4 -benzyl-5-hydroxymethyl-oxazolidin-2-one, m.p. 167.3°–168.9° C., $[\alpha]_D^{20}$: –79.4° (1% in methanol).

B) Analogously to Example 8A), from the 92:8 mixture of the (4S,5S) and (4S,5R) isomers from Example 7A) there is obtained in 75% yield 99% (4S,5S)-4-benzyl-5-hydroxymethyl-oxazolidin-2-one, m.p. 167°–169° C.

EXAMPLE 9

(6→VII, $R^1$=CH$_3$)

A solution of 4.7 ml of methanesulphonyl chloride in 10 ml of acetone is added at 25° C. to a suspension of 10.4 g of the alcohol from Example 8 in 20 ml of acetone and 6.1 ml of N-methylmorpholine and the suspension is stirred at 25° C. for 3 hours. A further 1.1 ml of N-methylmorpholine are added and the mixture is stirred for 1 hour. The suspension is shaken with 80 ml of semi-saturated NaHCO$_3$ solution and ethyl acetate and the separated aqueous phase is extracted with ethyl acetate. The ethyl acetate extracts are washed with water, dried and filtered. The filtrate is concentrated to give 14.3 g (100%) of crude methanesulphonic acid (4S,5S)-4-benzyl-2-oxo-oxazolidin-5-ylmethyl ester, TLC (SiO$_2$ ethyl acetate): $R_f$=0.4; MS (EI): 286 (M+H$^+$).

EXAMPLE 10

(6→VII, R$^1$=o-NO$_2$C$_6$H$_4$)

Analogously to Example 9, from 50 g of the alcohol from Example 8 and 80 g of o-nitrobenzenesulphonyl chloride there are obtained 88.2 g (93%) of o-nitrobenzenesulphonic acid (4S,5S)-4-benzyl-2-oxo-oxazolidin- 5-ylmethyl ester, TLC (SiO$_2$, ethyl acetate): R$_f$=0.38; MS (EI): 393 (M+M$^+$).

EXAMPLE 11

(6→VII, R$^1$=p-tolyl)

5.6 ml of triethylamine are added at 22° C. to a stirred suspension of 5.55 g of the alcohol from Example 8 in 27 ml of acetone and 6.64 g of p-toluenesulphonyl chloride and stirred at 22° C. for 6.5 hours. The suspension is treated with water, stirred at 10° C., filtered, the residue is washed with a water/acetone solution (3:2) and dried to give 9.09 g (94%) of 99% p-toluenesulphonic acid (4S,5S)-4-benzyl-2-oxo-oxazolidin- 5-ylmethyl ester, m.p. 148.7°–150.3° C., [α]$_D^{20}$: +3.0° (1% acetone).

EXAMPLE 12

(6→VII, R$^1$=p-NO$_2$C$_6$H$_4$)

15.4 g of p-nitrobenzenesulphonyl chloride are added in portions at 20°–25° C. to a stirred suspension of 12.0 g of the alcohol from Example 8 in 35 ml of THF and 7.66 ml of N-methylmorpholine and stirred for 4.5 hours. The suspension is again treated with 0.77 ml of N-methylmorpholine and stirred at 22° C. for 4.5 hours. The mixture is treated with 70 ml of a 2% sodium bicarbonate solution, stirred for 1.5 hours, filtered, the residue is washed with water and ethanol and dried to give 21.4 g (94%) of 98.5% p-nitrobenzenesulphonic acid (4S,5S)-4 -benzyl-2-oxo-oxazolidin-5-ylmethyl ester, m.p. 148°–149.5° C., [α]$_D^{20}$: +10.0° (1% in acetone).

EXAMPLE 13

(6→VII, R$^1$=p-BrC$_6$H$_4$)

Analogously to Example 12, from 35 g of the alcohol product from Example 8 and 56.1 g of p-bromobenzenesulphonyl chloride there are obtained 65.5 g (91%) of p-bromobenzenesulphonic acid (4S,5S)-4 -benzyl-2-oxo-oxazolidin-5-ylmethyl ester, m.p. 151.6°–153° C.

EXAMPLE 14

(1→II; R$^3$=Ac)

A solution of 5 g of 3-phenyl-2(S)-phthalimidopropan-1-al and 3.66 g of acetic anhydride in 30 ml of CH$_2$Cl$_2$ is added dropwise at 0° C. while stirring to a mixture of 1.76 g of NaCN and 0.16 g of benzyltriethylammonium chloride in 30 ml of CH$_2$Cl$_2$ and 55 ml of water and stirred at 0° C. for a further 7 hours. The aqueous phase is extracted with CH$_2$Cl$_2$. The extracts are dried, filtered and the filtrate is concentrated. The residue is chromatographed on silica gel with CH$_2$Cl$_2$:isopropanol (100:1). There are obtained 6.12 g (98%) of a 75:25 mixture of (2S,3S)- and (2R,3S)-3-(1,3-dioxo-1,3-dihydroisoindol-2-yl)- 2-acetoxy-4-phenylbutyronitrile, IR (film): 2227w (CN), 1773s, 1760s and 1717s (C=O from imide and acetate).

EXAMPLE 15

(1→II; R$^3$=benzyl-OCO, H)

A) A solution of 11.16 g of 3-phenyl-2(S)-phthalimidopropan-1-al and 0.7 g of benzyltriethylammonium chloride in 70 ml of CH$_2$Cl$_2$ is treated with 6.2 ml of benzyl chloroformate at –10° C. while stirring. A solution of 3.10 g of NaCN in 50 ml of H$_2$O is then added dropwise. After 0.5 hour at –10° C. the mixture is warmed to 0° C. The CH$_2$Cl$_2$ phase is washed with water and with saturated NaCl solution. The aqueous phase is extracted with CH$_2$Cl$_2$. The CH$_2$Cl$_2$ phases are dried, filtered and the filtrate is concentrated. The residue contains 18.33 g of a 70:30 mixture of (2S,3S)- and (2R,3S)-3-(1,3-dioxo-1,3 -dihydroisoindol-2-yl)-2-benzyloxycarbonyloxy-4-phenylbutyronitrile, MS (EI): 349 (6, M$^+$_–C$_6$H$_5$CH$_2$), 288 (6, M$^+$_–C$_6$H$_5$CH$_2$OCOOH), 91 (100, C$_6$H$_5$CH$_2$); IR (film): 2240w (CN), 1763s and 1717s (C=O from imide and carbamate).

B) A suspension of 2 g of the benzyl carbonate from A) and 0.15 g of Pd/C (10%) in 12 ml of ethanol and 2 ml of CH$_2$Cl$_2$ is hydrogenated at 22° C. for 2 hours, then filtered, washed with CH$_2$Cl$_2$ and the filtrate is concentrated. There are obtained 1.35 g (97%) of a 73:27 mixture of (2S,3S)- and (2R,3S)-3-(1,3-dioxo-1,3-dihydroisoindol-2-yl)-2 -hydroxy-4-phenylbutronitrile, IR (KBr): 3450m (OH), 2250w (C≡N), 1775m and 1712s (C=O from imide).

EXAMPLE 16

(1→II; R$^3$=H)

A suspension of 5 g of 3-phenyl-2(S)-phthalimidopropan-1-al and 4.43 g of ZnBr$_2$ in 50 ml of CH$_2$Cl$_2$ is treated at –15° C. while stirring with a solution of 1.95 g of trimethylsilyl cyanide in 5 ml of CH$_2$Cl$_2$ and stirred at –15° C. for 5 hours. The silyl ether formed is cleaved by the addition of a solution of 5 g of citric acid in 50 ml of ethanol at –10° C. The mixture is concentrated and the residue is treated with H$_2$O and extracted with CH$_2$Cl$_2$. The organic extracts are dried, filtered and the filtrate is concentrated. The residue contains 5.45 g (99%) of crude 3-(1,3-dioxo-1,3-dihydroisoindol-2-yl)-2-hydroxy-4-phenylbutyroronitrile as a 74:26 mixture of (2S,3S) and (2R,3S), IR (KBr): 3437m (OH), 2250w (C≡N), 1775m and 1713s (C=O from imide).

EXAMPLE 17

(II, R$^3$=H, via 1)

A) A suspension of 82.6 g of L-phenylalanine and 74.1 g of phthalic anhydride in 600 ml of toluene is heated under argon and under reflux for 8 hours. The resulting suspension is cooled to 22° C. and treated with 0.5 ml of DMF, followed by 66.64 g of oxalyl chloride. After stirring for 2 hours argon is blown into the suspension.

B) The solution containing the 3-phenyl-2(S)-phthalimidopropionyl chloride is diluted with 500 ml of toluene and treated with 72.11 g of 1,2-butylene oxide. 23.5 g of Pd/C (5%) and 100 ml of toluene are added to the solution. The suspension is hydrogenated for 17 hours while stirring, then filtered and the residue is washed with 200 ml of toluene.

C) A solution of 95.05 g of sodium pyrosulphite in 1 l of water is added at 22° C. while stirring to the solution containing the 3-phenyl-2(S)-phthalimidopropan- 1-al. After stirring for 4.5 hours the aqueous phase containing the addition product of bisulphite and the above aldehyde is washed with toluene. The toluene phases are extracted with water. 1200 ml of $CH_2Cl_2$ are added to the aqueous phases and the mixture is treated at 22° C. while stirring with a solution of 41.66 g of NaCN in 330 ml of water. After stirring for 1.2 hours water is added. The separated aqueous phase is extracted with $CH_2Cl_2$. The organic phases are dried, filtered and the residue is washed with $CH_2Cl_2$. The filtrates are evaporated and the residue is dissoved in 200 ml of $CH_2Cl_2$. 600 ml of hexane are added to the solution at 30° C. while stirring and then a further 600 ml of hexane are added at 0° C. The suspension is filtered, the residue is washed with hexane and then dried. There are obtained 114.02 g (74%) of a 74.7:23.5:1.4:0.4 mixture of the (2S, 3S):(2R,3S):(2R,3R):(2S,3R) isomers of 3-(1,3-dioxo-1,3 -dihydroisoindol-2-yl)-2-hydroxy-4-phenylbutyronitrile, m.p. 127.2°– 130.5° C., $[\alpha]_D^{20}$: –146.6° (1% in $CH_2Cl_2$).

EXAMPLE 18

(I→II, $R^3$=H)

A solution of 47.5 g of sodium pryrosulphite in 500 ml of water is added at 22° C. while stirring to the solution containing the product from Example 17B, i.e. 3-phenyl-2(S)-phthalimidopropan-1-al. After stirring for 7.5 hours the aqueous phase containing the addition product of pyrosulphite and the above aldehyde is washed with toluene. The toluene phases are extracted with water. A solution of 24.2 g of NaCN in 200 ml of water is added at 25° C. while stirring to the aqueous phases. The suspension is filtered after stirring for 1 hour and the residue is washed neutral with water. After drying there are obtained 112.03 g (73%) of a 67.2:32.8 mixture of the (2S,3S):(2R,3S) isomers of 3-(1,3-dioxo-1,3-dihydroisoindol-2-yl)-2-hydroxy-4-phenylbutyronitrile, m.p. 131°–133° C., $[\alpha]_D^{20}$: –150.2° (1% in $CH_2Cl_2$).

EXAMPLE 19

(II→III, $R^2$=$CH_3$, $R^3$=$R^4$=H)

A) A solution of 100 g of 3-(1,3-dioxo-1,3-dihydroisoindol-2-yl)-2 -hydroxy-4-phenylbutyronitrile (Example 17C) in 450 ml of $CH_2Cl_2$ is added at 0° C. to a solution of 400 g of HCl in 980 ml of methanol. After stirring at 0° C. for 18 hours the suspension is filtered. A mixture of 600 ml of ethyl acetate and 600 ml of water is added to the residue containing the resulting imino ether.HCl. After the solid has dissolved the aqueous phase is extracted with ethyl acetate. The organic phases are washed with saturated $NaHCO_3$ solution and with water and then dried. The suspension is filtered and the filtrate is evaporated to give 77.15 g (70%) of a 93:7 mixture of the (2S,3S):(2R,3S) isomers of methyl 3-(1,3-dioxo-1,3-dihydroisoindol-2-yl)-2-hydroxy-4-phenylbutyrate, $[\alpha]_D^{20}$: –121.5° (1% in ethyl acetate).

B) 120 g of HCl are introduced at 0° C. into a solution of 200 g of 3 -(1,3-dioxo-1,3-dihydroisoindol-2-yl)-2-hydroxy-4-phenylbutyronitrile (Example 17C) in 1200 ml of toluene and 106 ml of methanol and stirred at 0° C. for 3 hours. The suspension is treated with 1200 ml of water and 400 ml of methanol and stirred at 22° C. for 2 hours. The aqueous phase is extracted with toluene. The organic phases are washed with water, dried, filtered and the filtrate is evaporated to give 221 g (100%) of a 75:25 mixture of the (2S,3S):(2R,3S) isomers of methyl 3-(1,3-dioxo-1,3-dihydroisoindol-2-yl)-2-hydroxy-4-phenylbutyrate, $[\alpha]_D^{20}$: –133.1° (1% in ethyl acetate).

EXAMPLE 20

(II→III, $R^2$=$C_2H_5$, $R^3$=$R^4$=H)

150 ml of HCl-saturated ethanol is treated at 0° C. with a solution of 30 g of 3-(1,3-dioxo-1,3-dihydroisoindol-2-yl)-2-hydroxy-4-phenylbutyronitrile (Example 17C) in 150 ml of $CH_2Cl_2$. After 4 hours at 0° C. the suspension is diluted with 150 ml of $CH_2Cl_2$, filtered and the residue is washed with $CH_2Cl_2$. In order to hydrolyze the imino ether.HCl formed, the residue is taken up in 250 ml of toluene, 250 ml of water and 12 ml of ethanol. After stirring for 4 hours the aqueous phase is extracted with toluene and the toluene phases are washed with water. The toluene phases are dried, filtered and the filtrate is concentrated. The residue contains 19.54 g (57%) of a 95:5 mixture of ethyl (2S,3S)- and (2R,3S)-3-(1,3-dioxo-1,3-dihydroisoindol-2-yl)-2-hydroxy-4-phenylbutyrate, m.p. 83.1°–84.3° C., $[\alpha]_D^{20}$: –143.1° (1% in ethyl acetate).

EXAMPLE 21

(II→III, $R^2$=i-Pr, $R^3$=$R^4$=H)

A) 150 ml of HCl-saturated isopropanol are treated at 0° C. while stirring with a solution of 30 g of 3-(1,3-dioxo-1, 3-dihydro-isoindol- 2-yl)-2-hydroxy-4-phenylbutyronitrile from Example 17 C) in 150 ml of $CH_2Cl_2$. After 9 hours at 0° C. the solution is treated with 300 ml of $H_2O$ and stirred at 22° C. for 4 hours. The phases are separated and the aqueous phase is extracted with $CH_2Cl_2$. The organic extracts are washed with water, dried, filtered and the filtrate is concentrated. The residue contains 29.73 g (83%) of a 70:30 mixture of the (2S,3S) and (2R,3S) isomers of isopropyl 3-(1,3-dioxo-1,3-dihydroisoindol-2 -yl)-2-hydroxy-4-phenylbutyrate $[\alpha]_D^{20}$=126.8° (1% in ethyl acetate); MS (EI): 368 (1,$M+H^+$), 250 [100, M-CH(OH)COOCH($CH_3$)$_2$].

B) The isomer mixture from A) is dissolved in 180 ml of t-butyl methyl ether, treated with 60 ml of hexane, stirred at 22° C. and then at 0° C. and –10° C. and filtered. After drying there are obtained 13.13 g (36.5%) of isopropyl (2S,3S)-3-(1,3-dioxo-1,3-dihydroisoindol-2-yl)- 2-hydroxy-4-phenylbutyrate, IR (film): 3463m (OH), 1773m, 1730s and 1705s (C=O from imide and ester).

EXAMPLE 22

(II→III, $R^2$=$CH_3$, $R^3$=Ac, $R^4$=H)

A solution of 3.39 g of a 75:25 mixture of (2S,3S)- and (2R,3S)-3 -(1,3-dioxo-1,3-dihydroisoindol-2-yl)-2-acetoxy-4-phenylbutyronitrile (Example 14) in 25 ml of methanol is saturated with HCl at 0° C. and stirred at 0° C. for 21 hours. The solution is treated with 100 ml of water and extracted with ethyl acetate. The extracts are dried, filtered and the filtrate is concentrated. The residue contains 3.3 g (100%) of a 75:25 mixture of the (2S,3S):(2R,3S) isomers of methyl 3-( 1,3-dioxo-1,3-dihydroisoindol-2-yl)-2-hydroxy-4-phenylbutyrate, IR (film): 3362m (OH), 1775m, 1745s and 1712s (C=O from imide and ester).

EXAMPLE 23

(III→IV, $R^2$=$CH_3$)

A) A solution of 20 g of a 93:7 mixture of the (2S,3S):(2R, 3S) isomers of methyl 3-(1,3-dioxo-1,3-dihydroisoindol-2-yl)-2-hydroxy-4-phenylbutyrate (Example 19A) in 20 ml of methanol is treated at 0° C. while stirring with a solution of 11.75 ml of a 18.7% solution of methylamine in methanol and stirred at 0° C. for 4 hours.

44 ml of a 20% solution of HCl in methanol is added to the solution at 0° C. After stirring at 22° C. for 3 hours the suspension is filtered, the residue is washed with methanol and the filtrate is concentrated. The pH of the residue is adjusted to 4 with dilute ammonia solution at 0° C. The aqueous phase is washed with ethyl acetate, the organic phase is extracted with water and the pH of the combined aqueous phases is adjusted to 9.3 with ammonia solution at 22° C. The aqueous phase is extracted several times with ethyl acetate, the organic phases are dried, filtered and the filtrate is concentrated to 50 g. The residual solution is treated with 3.4 ml of acetic acid and stirred at 0° C. The suspension is filtered and the residue is washed with ethyl acetate. After drying there are obtained 13.83 g (87%) of a 98:2 mixture of the (2S,3S) and (2R,3S) isomers of methyl 3-amino-2 -hydroxy-4-phenylbutyrate acetate m.p. 113°–114.5° C., $[\alpha]_D^{20}$: +15.3° (1% in methanol).

B) Analogously to Example 23A, by reacting 54.6 g of a 75:25 mixture of the (2S,3S):(2R,3S) isomers of methyl 3-(1,3 dioxo-1,3 -dihydroisoindol-2-yl)-2-hydroxy-4-phenylbutyrate (Example 19B) there are obtained 28.4 g (66%) of a 92:8 mixture of the (2S,3S) and (2R,3S) isomers of methyl 3-amino-2-hydroxy-4-phenylbutyrate acetate, m.p. 109°–110° C., $[\alpha]_D^{20}$: +13.6° (1% in methanol).

EXAMPLE 24

(III→IV, $R^2=C_2H_5$)

Analogously to Example 23, by reacting a solution of 10.42 g of a 95:5 mixture of the (2S,3S) and (2R,3S) isomers of ethyl 3-(1,3-dioxo- 1,3-dihydroisoindol-2-yl)-2-hydroxy-4-phenylbutyrate (Example 20) in 10 ml of ethanol with 5.9 ml of a 33% solution of methylamine in ethanol there are obtained 5.39 g (82%) of ethyl (2S,3S)-3-amino-2 -hydroxy-4-phenylbutyrate, TLC (SiO$_2$, CH$_2$Cl$_2$/methanol 10:1, UV$_{254}$): R$_f$=0.34.

I claim:

1. The compound (2S,3S)-3-(1,3-dioxo-1,3-dihydroisoindol-2-yl)-2 -acetoxy-4-phenylbutyronitrile or acid-addition salts thereof.

2. The compound (2S,3S)-3-(1,3-dioxo-1,3-dihydroisoindol-2-yl)-2 -benzyloxycarbonyloxy-4-phenylbutyronitrile or acid-addition salts thereof.

* * * * *